United States Patent [19]

Brown et al.

[11] Patent Number: 4,745,060

[45] Date of Patent: May 17, 1988

[54] METHODS AND COMPOSITIONS FOR THE DETECTION OF FAMILIAL HYPERCHOLESTEROLEMIA

[75] Inventors: Michael S. Brown; Joseph L. Goldstein; David W. Russell, all of Dallas, Tex.

[73] Assignee: Board of Regents, The University of Texas System, Austin, Tex.

[21] Appl. No.: 687,087

[22] Filed: Dec. 28, 1984

[51] Int. Cl.[4] .................. C12N 15/00; C12N 1/20; C12Q 1/68; C07H 21/00

[52] U.S. Cl. ........................ 435/172.3; 435/6; 435/320; 435/253; 536/27; 935/9; 935/27; 935/72; 935/78

[58] Field of Search .............. 435/6, 172.3, 253, 317, 435/803, 320; 536/27; 436/501, 811; 935/9, 27, 31, 78, 72

[56] References Cited

U.S. PATENT DOCUMENTS 4,358,535 11/1982 Falkow et al. .
4,395,486 7/1983 Wilson et al. ................. 436/508

FOREIGN PATENT DOCUMENTS 0126544 11/1984 European Pat. Off. .

OTHER PUBLICATIONS

Wieringa, B. et al, *Nucleic Acids Research*, vol. 9, No. 3, 1981, pp. 489–501.
Lehrman, M. A. et al., *Science*, vol. 227, 1985, pp. 140–146.
Sauls, C. D. et al, *Clin Chem.*, vol. 31, No. 6, 1985, pp. 804–811.
Palmiter, R. D., (1974) "Magnesium Precipitation of Ribonucleoprotein Complexes, Expedient Techniques for the Isolation of Undergrated Polysomes & Messenger Ribonucleic Acid," *Biochemistry*, 13:3606–3615.
Pelham, R. B. & Jackson, R. J., (1976) "An Efficient mRNA-Dependent Translation System from Reticulocyte Lysates" *Eur. J. Biochem.*, 67:247–256.
Sanger, F., Nicklen, S. and Coulson, A. R. (1977), "DNA Sequencing with Chain-Terminating Inhibitors," *Proc. Natl. Acad. Sci. U.S.A.*, 74:5463–5467.
Lawn, R. M., Fritsch, E. F., Parker, R. C., Blake, G. and Maniatis, T. (1978), "The Isolation and Characterization of Linked Gamma-and Beta-Globin Genes from a Cloned Library of Human DNA," *Cell*, 15:1157–1174.
Maxam, A. M. and Gilbert, W. (1980), "Sequencing End-Labelled DNA with Base-Specific Chemical Cleavages," *Meth. Enzym.*, 65:499–560.
Okayama, H. and Berg, P. (1982), "High-Efficiency Cloning of Full-Linked cDNA," *Mol. Cell. Biol.*, 2:161–170.
Goldstein, J. L. and Brown, M. S. (1982), "The LDL Receptor Defect and Familial Hypercholesterolemia," *Medical Clinics of North America*, 66:335–362.
Schneider, W. J., Beisiegel, U., Goldstein, J. L. and Brown, M. S. (1982), "Purification of the Low Density Lipoprotein Receptor, and Acidic Glycoprotein of 164,000 Molecular Weight," *Jrnl. Biol. Chem.*, 257:2664–2673.
Tolleshaug, H., Goldstein, J. L., Schneider, W. J. and Brown, M. S. (1982), "Posttranslational Processing of the LDL Receptor and its Genetic Distribution in Familial Hypercholesterolemia," *Cell*, 30:715–724.
Maniatis, T. (1982), *Molecular Cloning*, Cold Spring Harbor Laboratory, Cold Spring Harbor, N.Y., pp. 196, 250, 251, 316, 317, 326–328, 509–511, 514, 519.

(List continued on next page.)

Primary Examiner—Charles F. Warren
Assistant Examiner—Jeremy M. Jay
Attorney, Agent, or Firm—Arnold, White & Durkee

[57] ABSTRACT

Recombinant DNA transfer vectors containing DNA inserts which are complementary to either the human LDL receptor gene, or its mRNA transcript, are disclosed. Also disclosed are methods which utilize these genetic probes for diagnosing Familial Hypercholesterolemia (FH) in a suspected individual. A case study of one such individual, FH 274, is disclosed wherein the genetic deletion mutation is detailed with great precision through the practice of this invention.

21 Claims, 8 Drawing Sheets

OTHER PUBLICATIONS

Okayama, H. and Berg, P. (1983), "A cDNA Cloning Vector that Permits Expression of cDNA Inserts in Mammalian Cells," *Mol. Cell Biol.*, 3:280–289.

Schneider, W. J., Brown, M. S. and Goldstein, J. L. (1983), "Kinetic Defects in the Processing of the Low Density Lipoprotein Receptor in Fibroblasts from WHHL Rabbits and a Family with Familial Hypercholesterolemia," *Mol. Biol. Med.*, 1:353–367.

Tolleshaug, H., Hobgood, K. K., Brown, M. S. and Goldstein, J. L. (1983), "The LDL Receptor Locust and Familial Hypercholesterolemia: Multiple Mutations Disrupt Transport and Processing of a Membrane Receptor," *Cell*, 32:941–951.

Feinberg, A. P. and Vogelstein, B. (1983), "A Technique for Radio Labelling DNA Restriction Endonuclease Fragments to High Specific Activity," *Analyt, Biochem.*, 132:6–13.

Messing, J. (1983), "New M13 Vectors for Cloning" *Meth. Enzymol.*, 101:20–37, 50.

Russell, D. W., Yamamoto, G., Schneider, W. J., Slaughter, C. J., Brown, M. S. and Goldstein, J. L. (1983), "cDNA Cloning of the Bovine Low Density Lipoprotein Receptor: Feedback Regulation of a Receptor mRNA," *Proc. Natl. Acad. Sci. U.S.A.*, 80:7501–7505.

Church, G. M. and Gilbert, W. (1984), "Genomic Sequencing," *Proc. Natl. Acad. Sci. U.S.A.*, 81:1991–1995.

Russell, D. W., Schneider, W. J., Yamamoto, T., Luskey, K. L., Brown, M. S. and Goldstein, J. L. (1984), "Domain Map of the LDL Receptor: Sequence Homology with the Epidermal Growth Factor Precursor," *Cell*, 37:577–585.

Yamamoto, T., Davis, C. G., Brown, M. S., Schneider, W. J., Casey, M. L., Goldstein, J. L. and Russell, D. W. (1984), "The Human LDL Receptor: A Cysteine-Rich Protein with Multiple Alu Sequences in its mRNA," *Cell*, 39:27–28.

Fig. 3A

```
GCAGTGGGCGACAGATGTGAAAGAAACGAGTTCCAGTGCCAAGACGGGAAATGCATCTCCTACAAGTGGGTCTGCGATGGCAGCGCTGAGTGG
AlaValGlyAspArgCysGluArgAsnGluPheGlnCysGlnAspGlyLysCysIleSerTyrLysTrpValCysAspGlySerAlaGluCys
1                     10                    20                    30

TGCATTCCTCAGTTCTGGAGGTGCGATGGCCAAGTGGACTGCGACAACGGCTCAGACGAGCAAGGCTGTCCCCCCAAGACGTGCTCCCAGGAC
CysIleProGlnPheTrpArgCysAspGlyGlnValAspCysAspAsnGlySerAspGluGlnGlyCysProProLysThrCysSerGlnAsp
61                    70                    80                    90

TCCTGCCGGTGCTCACCTGTGGTCCCGCCAGCTTCCAGTGCAACAGCTCCACCTGCATCCCCCAGCTGTGGGCCTGCGACAACGACCCCGAC
SerCysProValLeuThrCysGlyProAlaSerPheGlnCysAsnSerSerThrCysIleProGlnLeuTrpAlaCysAspAsnAspProAsp
121                   130                   140                   150

TTCCACTGCCTAAGTGGCGAGTGCATCCACTCCAGCTGGCGCTGTGATGGTGGCCCCGACTGCAAGGACAAATCTGACGAGGAAAACTGCGCT
PheHisCysLeuSerGlyGluCysIleHisSerSerTrpArgCysAspGlyGlyProAspCysLysAspLysSerAspGluGluAsnCysAla
181                   190                   200                   210

AAGGACATGAGCGATGAAGTTGGCTGCGTTAATGTGACACTCTGCGAGGGACCCAACAAGTTCAAGTGTCACAGCGGCGAATGCATCACCCTG
LysAspMetSerAspGluValGlyCysValAsnValThrLeuCysGluGlyProAsnLysPheLysCysHisSerGlyGluCysIleThrLeu
241                   250                   260                   270

AACGGCGGCTGTTCCCACGTCTGCAATGACCTTAAGATCGGCTACGAGTGCCTGTGCCCCGACGGCTTCCAGCTGGTGGCCCAGCGAAGATGC
AsnGlyGlyCysSerHisValCysAsnAspLeuLysIleGlyTyrGluCysLeuCysProAspGlyPheGlnLeuValAlaGlnArgArgCys
301                   310                   320                   330

GGCTTCCAGCTGGACCCCCACACGAAGGCCTGCAAGGCTGTGGGCTCCATCGCCTACCTCTTCTTCACCAACCGGCACGAGGTCAGGAAGATG
GlyPheGlnLeuAspProHisThrLysAlaCysLysAlaValGlySerIleAlaTyrLeuPhePheThrAsnArgHisGluValArgLysMet
361                   370                   380                   390

TACTGGTCTGACCTGTCCCAGAGAATGATCTGCAGCACCCAGCTTGACAGAGCCCACGGCGTCTCTTCCTATGACACCGTCATCAGCAGGGAC
TyrTrpSerAspLeuSerGlnArgMetIleCysSerThrGlnLeuAspArgAlaHisGlyValSerSerTyrAspThrValIleSerArgAsp
421                   430                   440                   450

GATACCAAGGGCGTGAAGAGGAAAACGTTATTCAGGGAGAACGGCTCCAAGCCAAGGGCCATCGTGGTGGATCCTGTTCATGGCTTCATGTAC
AspThrLysGlyValLysArgLysThrLeuPheArgGluAsnGlySerLysProArgAlaIleValValAspProValHisGlyPheMetTyr
481                   490                   500                   510

TGGCCCAATGGCATCACCCTAGATCTCCTCAGTGGCCGCCTCTACTGGGTTGACTCCAAACTTCACTCCATCTCAAGCATCGATGTCAATGGC
TrpProAsnGlyIleThrLeuAspLeuLeuSerGlyArgLeuTyrTrpValAspSerLysLeuHisSerIleSerSerIleAspValAsnGly
541                   550                   560                   570

GATATCATCAACGAAGCCATTTTCAGTGCCAACCGCCTCACAGGTTCCGATGTCAACTTGTTGGCTGAAAACCTACTGTCCCCAGAGGATATG
AspIleIleAsnGluAlaIlePheSerAlaAsnArgLeuThrGlySerAspValAsnLeuLeuAlaGluAsnLeuLeuSerProGluAspMet
601                   610                   620                   630
```

Fig. 3B

```
       -13        1
          AGAGGCTGCGAGCATGGGGCCCTGGGGCTGGAAATTGCGCTGGACCGTCGCCTTGCTCCTCGCCGCGGCGGGGACT   83
                    MetGlyProTrpGlyTrpLysLeuArgTrpThrValAlaLeuLeuLeuAlaAlaAlaGlyThr
                         -20                    -10                    -1

CAGGATGGCTCTGATGAGTCCCAGGAGACGTGCTTGTCTGTCACCTGCAAATCCGGGGACTTCAGCTGTGGGGGCCGTGTCAACCGC   243
GlnAspGlySerAspGluSerGlnGluThrCysLeuSerValThrCysLysSerGlyAspPheSerCysGlyGlyArgValAsnArg
              40                    50                    60                    80

GAGTTTCGCTGCCACGATGGGAAGTGCATCTCTCGGCAGTTCGTCTGTGACTCAGACCGGGACTGCTTGGACGGCTCAGACGAGGCC   423
GluPheArgCysHisAspGlyLysCysIleSerArgGlnPheValCysAspSerAspArgAspCysLeuAspGlySerAspGluAla
              100                   110                   120

TGCGAAGATGGCTCGGATGAGTGGCCGCAGCGCTGTAGGGGTCTTTACGTGTTCCAAGGGGACAGTAGCCCCTGCTCGGCCTTCGAG   603
CysGluAspGlySerAspGluTrpProGlnArgCysArgGlyLeuTyrValPheGlnGlyAspSerSerProCysSerAlaPheGlu
              160                   170                   180

GTGGCCACCTGTCGCCCTGACGAATTCCAGTGCTCTGATGGAAACTGCATCCATGGCAGCCGGCAGTGTGACCGGGAATATGACTGC   783
ValAlaThrCysArgProAspGluPheGlnCysSerAspGlyAsnCysIleHisGlySerArgGlnCysAspArgGluTyrAspCys
              220                   230                   240

GACAAAGTCTGCAACATGGCTAGAGACTGCCGGGACTGGTCAGATGAACCCATCAAAGAGTGCGGGACCAACGAATGCTTGGACAAC   963
AspLysValCysAsnMetAlaArgAspCysArgAspTrpSerAspGluProIleLysGluCysGlyThrAsnGluCysLeuAspAsn
              280                   290                   300

GAAGATATCGATGAGTGTCAGGATCCCGACACCTGCAGCCAGCTCTGCGTGAACCTGGAGGGTGGCTACAAGTGCCAGTGTGAGGAA   1143
GluAspIleAspGluCysGlnAspProAspThrCysSerGlnLeuCysValAsnLeuGluGlyGlyTyrLysCysGlnCysGluGlu
              340                   350                   360

ACGCTGGACCGGAGCGAGTACACCAGCCTCATCCCCAACCTGAGGAACGTGGTCGCTCTGGACACGGAGGTGGCCAGCAATAGAATC   1323
ThrLeuAspArgSerGluTyrThrSerLeuIleProAsnLeuArgAsnValValAlaLeuAspThrGluValAlaSerAsnArgIle
              400                   410                   420

ATCCAGGCCCCCGACGGGCTGGCTGTGGACTGGATCCACAGCAACATCTACTGGACCGACTCTGTCCTGGGCACTGTCTCTGTTGCG   1503
IleGlnAlaProAspGlyLeuAlaValAspTrpIleHisSerAsnIleTyrTrpThrAspSerValLeuGlyThrValSerValAla
              460                   470                   480

TGGACTGACTGGGGAACTCCCGCCAAGATCAAGAAAGGGGGCCTGAATGGTGTGGACATCTACTCGCTGGTGACTGAAAACATTCAG   1683
TrpThrAspTrpGlyThrProAlaLysIleLysLysGlyGlyLeuAsnGlyValAspIleTyrSerLeuValThrGluAsnIleGln
              520                   530                   540

GGCAACCGGAAGACCATCTTGGAGGATGAAAAGAGGCTGGCCCACCCCTTCTCCTTGGCCGTCTTTGAGGACAAAGTATTTTGGACA   1863
GlyAsnArgLysThrIleLeuGluAspGluLysArgLeuAlaHisProPheSerLeuAlaValPheGluAspLysValPheTrpThr
              580                   590                   600

GTCCTCTTCCACAACCTCACCCAGCCAAGAGGAGTGAACTGGTGTGAGAGGACCACCCTGAGCAATGGCGGCTGCCAGTATCTGTGC   2043
ValLeuPheHisAsnLeuThrGlnProArgGlyValAsnTrpCysGluArgThrThrLeuSerAsnGlyGlyCysGlnTyrLeuCys
              640                   650                   660
```

```
CTCCCTGCCCCGCAGATCAACCCCCACTCGCCCAAGTTTACCTGCGCCTGCCCGGACGGCATGCTGCTGGCCAGGGACATGAGGAGCTGCCTC
LeuProAlaProGlnIleAsnProHisSerProLysPheThrCysAlaCysProAspGlyMetLeuLeuAlaArgAspMetArgSerCysLeu
661                    670                    680                    690
ACCACCCGGCCTGTTCCCGACACCTCCCGGCTGCCTGGGGCCACCCCTGGGCTCACCACGGTGGAGATAGTGACAATGTCTCACCAAGCTCTG
ThrThrArgProValProAspThrSerArgLeuProGlyAlaThrProGlyLeuThrThrValGluIleValThrMetSerHisGlnAlaLeu
721                    730                    740                    750
CTTTGCCTGGGGGTCTTCCTTCTATGGAAGAACTGGCGGCTTAAGAACATCAACAGCATCAACTTTGACAACCCCGTCTATCAGAAGACCACA
LeuCysLeuGlyValPheLeuLeuTrpLysAsnTrpArgLeuLysAsnIleAsnSerIleAsnPheAspAsnProValTyrGlnLysThrThr
781                    790                    800                    810
ACATCTGCCTGGAGTCCCGCCCCTGCCCAGAACCCTTCCTGAGACCTCGCCGGCCTTGTTTTATTCAAAGACAGAGAAGACCAAAGCATTGCC
TGGTTTCTTCCTTTCCTGTGAAGGATAAGAGAAACAGGCCCGGGGCGACCAGGATGACACCTCCATTTCTCTCCAGGAAGTTTTGAGTTTCTC
GCAGATGGCACCAACGGGACCCCCTGGCCCTGCCTCATCCACCAATCTCTAAGCCAAACCCCTAAACTCAGGAGTCAACGTGTTTACCTCTTC
TACCTTCCTTAAGCCAGGAAAGGGATTCATGGCGTCGGAAATGATCTGGCTGAATCCGTGGTGGCACCGAGACCAAACTCATTCACCAAATGA
GACACGTGGCCTGCACCCAGGTGTGGCTGTCAGGACACCAGCCTGGTGCCCATCCTCCCGACCCCTACCCACTTCCATTCCCGTGGTCTCCTT
GGGATCCCAGGCCAGGGAAAGCCCGTGTCAATGAATGCCGGGGACAGAGAGGGGCAGGTTGACCGGGACTTCAAAGCCGTGATCGTGAATATC
TGTCGTTGATGGGTATGTGTTTAAAACATGCACGGTGAGCCGGGCGCAGTGGCCTCACGCCTGTAATCCCAGCACTTTGGGAGGCCGAGGCG
CGCGGTGGTGGGCACCTGTAGTCCCAGCTACTCGGGAGGCTGAGGCAGGAGAATGGTGTGAACCCGGGAAGCGGAGCTTGCAGTGAGCCGAGA
TGCATCAGCAGCCCATGGCCTCTGGCCAGGCATGGCGAGGCTGAGGTGGGAGGATGGTTTGAGCTCAGGCATTTGAGGCTGTCGTGAGCTATG
TGTAATCCCAGCACTTTGGGAGGCTGAGCTGGATCACTTGAGTTCAGGAGTTGGAGACCAGGCCTGAGCAACAAAGCGAGATCCCATCTCTAC
TGAGCCCAGGAGGTGGAGGTTGCAGTGAGCCATGATCGAGCCACTGCACTCCAGCCTGGGCAACACATGAAGACCCTATTTCAGAAATACAAC
ATGTCCGGAGAGACAGTGACAGCCTCCGTCAGACTCCCGCGTGAAGATGTCACAAGGGATTGGCAATTGTCCCCAGGGACAAAACACTGTGTC
TGTTTGCACTTTGTATATTGGTTGAAACTGTTATCACTTATATATATATATACACACATATATATAAAATCTATTTATTTTTTGCAAACCCTGG
TTTGCACGAACTGGACTGTGTGCAACGCTTTTTGGGAGAATGATGTCCCCGTTGTATGTATGAGTGGCTTCTGGGAGATGGGTGTCACTTTTT
```

*Fig. 3C*

```
ACAGAGGCTGAGGCTGCAGTGGCCACCCAGGAGACATCCACCGTCAGGCTAAAGGTCAGCTCCACAGCCGTAAGGACACAGCACACA   2223
ThrGluAlaGluAlaAlaValAlaThrGlnGluThrSerThrValArgLeuLysValSerSerThrAlaValArgThrGlnHisThr
            •••                •••  ••• •••                    •••          •••
            700                    710                             720
GGCGACGTTGCTGGCAGAGGAAATGAGAAGAAGCCCAGTAGCGTGAGGGCTCTGTCCATTGTCCTCCCCATCGTGCTCCTCGTCTTC   2403
GlyAspValAlaGlyArgGlyAsnGluLysLysProSerSerValArgAlaLeuSerIleValLeuProIleValLeuLeuValPhe
            760                    770                             780
GAGGATGAGGTCCACATTTGCCACAACCAGGACGGCTACAGCTACCCCTCGAGACAGATGGTCAGTCTGGAGGATGACGTGGCGTGA   2583
GluAspGluValHisIle(Cys)HisAsnGlnAspGlyTyrSerTyrProSerArgGlnMetValSerLeuGluAspAspValAla•••
                    820                       830
TGCCAGAGCTTTGTTTTATATATTTATTCATCTGGGAGGCAGAACAGGCTTCGGACAGTGCCCATGCAATGGCTTGGGTTGGGATTT   2763
TCCACCGTGACACAATCCTCAAACATGGAAGATGAAAGGGCAGGGGATGTCAGGCCCAGAGAAGCAAGTGGCTTTCAACACACAACA   2943
TATGCAAGCCTTGCTAGACAGCCAGGTTAGCCTTTGCCCTGTCACCCCCGAATCATGACCCACCCAGTGTCTTTCGAGGTGGGTTTG   3123
TGCCACTTCCCAGAGGCAGAGCCTGAGTCACCGGTCACCCTTAATATTTATTAAGTGCCTGAGACACCCGGTTACCTTGGCCGTGAG   3303
GCACTTTCTCAGTTCAGAGTTGTACACTGTGTACATTTGGCATTTGTGTTATTATTTTGCACTGTTTTCTGTCGTGTGTGTTGGGAT   3483
GAGAACTGCCATTGTCGTCTTTATGTCCGCCCACCTAGTGCTTCCACTTCTATGCAAATGCCTCCAAGCCATTCACTTCCCCAATCT   3663
GGTGGATCATGAGGTCAGGAGATCGAGACCATCCTGGCTAACAAGGTGAAACCCCGTCTCTACTAAAAATACAAAAAATTAGCCGGG   3843
TTGCGCCACTGCAGTCCGCAGTCTGGCCTGGGCGACAGAGCGAGACTCCGTCTCAAAAAAAACAAAACAAAAAAAAAACCATGCATGG   4023
ATTATGCCACTGCTTTCCAGCCTGGGCAACATAGTAAGACCCCATCTCTTAAAAAATGAATTTGGCAGACACAGGTGCCTCACGCC   4203
AAAAACCAAAAAGTTAAAAATCAGCTGGGTATGGTGGCACGTGCCTGTGATCCCAGCTACTTGGGAGGCTGAGGCAGGAGGATCGCC   4383
TATAAAAAAAATAAATAAATCCTCCAGTCTGGATCGTTTGACGGGACTTCAGGTTCTTTCTGAAATCGCCGTGTTACTGTTGCACTG   4563
CCCCCCAGTGCAGGGAACCGTGATAAGCCTTTCTGGTTTCGGAGCACGTAAATGCGTCCCTGTACAGATAGTGGGGATTTTTTGTTA   4743
TTGCTGTATTTGTTCAGTGACTATTCTCGGGGCCCTGTGTAGGGGGTTATTGCCTCTGAAATGCCTCTTCTTTATGTACAAAGATTA   4923
TAAACCACTGTATAGAAGGTTTTTGTAGCCTGAATGTCTTACTGTGATCAATTAAATTTCTTAAATGAAAAAAAAAAAAA$_n$    5103
```

Fig. 3D

METHODS AND COMPOSITIONS FOR THE DETECTION OF FAMILIAL HYPERCHOLESTEROLEMIA

BACKGROUND OF THE INVENTION

The government may own certain rights in the present invention pursuant to National Institutes of Health grant numbers HL20948 and HL31346.

The present invention is directed towards methods and compositions useful in the diagnosis of a genetic predisposition towards the development of hypercholesterolemia, atherosclerosis, and eventually, heart disease. More particularly, the present invention is directed towards recombinant DNA molecules which serve as useful probes in detecting the presence of mutant low density lipoprotein (LDL) receptor genes in individuals suspected of having familial hypercholesterolemia (FH).

Half of all deaths in the U.S. are caused by atherosclerosis, the disease in which cholesterol, accumulating in the wall of arteries, forms bulky plaques that inhibit the flow of blood until a clot eventually forms, obstructing an artery and causing a heart attack or a stroke. The cholesterol of atherosclerotic plaques is derived from particles called low-density lipoprotein (LDL) that circulate in the bloodstream. The more LDL there is in the blood, the more rapidly atherosclerosis develops.

Epidemiologic data reveal the surprising fact that more than half of the people in Western industrialized societies, including the U.S., have a level of circulating LDL that puts them at high risk for developing atherosclerosis. Because such concentrations are so prevalent, they are considered "normal," but clearly they are not truly normal. They predispose to accelerated atherosclerosis and heart attacks or strokes.

Some answers as to why the LDL levels are so dangerously high in many Americans are emerging from studies of specialized proteins, called LDL receptors. These receptors project from the surface of animal cells. The receptors bind LDL particles and extract them from the fluid that bathes the cells. The LDL is taken into the cells and broken down, yielding its cholesterol to serve each cell's needs. In supplying cells with cholesterol the receptors perform a second physiological function, which is critical to the prevention of atherosclerosis: they remove LDL from the bloodstream.

The number of receptors displayed on the surface of cells varies with the cells' demand for cholesterol. When the need is low, excess cholesterol accumulates; cells make fewer receptors and take up LDL at a reduced rate. This protects cells against excess cholesterol, but at a high price: the reduction in the number of receptors decreases the rate at which LDL is removed from the circulation, the blood level of LDL rises and atherosclerosis is accelerated.

It has been proposed that the high level of LDL in many Americans is attributable to a combination of factors that diminish the production of LDL receptors. Recognition of the central role of the receptors has led to a treatment for a severe genetic form of atherosclerosis, and it has also shed some light on the continuing controversy over the role of diet in atherosclerosis in the general population.

LDL is a large spherical particle whose oily core is composed of some 1,500 molecules of the fatty alcohol cholesterol, each attached by an ester linkage to a long-chain fatty acid. This core of cholesterol esters is enclosed in a layer of phospholipid and unesterified cholesterol molecules. The phospholipids are arrayed so that their hydrophilic heads are on the outside, allowing the LDL to be dissolved in the blood or intercellular fluid. Embedded in this hydrophilic coat is one large protein molecule designated apoprotein B-100.

It is apoprotein B-100 that is recognized and bound by the LDL receptor, a glycoprotein (a protein to which sugar chains are attached). The receptor spans the thickness of the cell's plasma membrane and carries a binding site that protrudes from the cell surface. Binding takes place when LDL is present at a concentration of less than $10^{-9}$ molar, which is to say that the receptor can pick out a single LDL particle from more than a billion molecules of water. The receptor binds only lipoproteins carrying apoprotein B-100 or a related protein designated apoprotein E.

In 1976 it was discovered that the LDL receptors are clustered in specialized regions where the cell membrane is indented to form craters known as coated pits (because the inner surface of the membrane under them is coated with the protein clathrin). Within minutes of their formation the pits pouch inward into the cell and pinch off from the surface to form membrane-bounded sacs called coated vesicles; and LDL bound to a receptor is carried into the cell. Receptor-mediated endocytosis, the term applied to this process of uptake through coated pits and vesicles, is now being recognized as a general mechanism whereby cells take up many large molecules, each having its own highly specific receptor.

Eventually the LDL is separated from the receptor (which is recycled to the cell surface) and is delivered to a lysosome, a sac filled with digestive enzymes. Some of the enzymes break down the LDL's coat, exposing the cholesterol ester core. Another enzyme clips off the fatty acid tails of the cholesterol esters, liberating unesterified cholesterol, which leaves the lysosome. All cells incorporate the cholesterol into newly synthesized surface membranes. In certain specialized cells the cholesterol extracted from LDL has other roles. In the adrenal gland and in the ovary it is converted into respectively the steroid hormones cortisol and estradiol; in the liver it is transformed to make bile acids, which have a digestive function in the intestine.

The central role of the LDL receptor in atherosclerosis was first appreciated in 1974 when it was shown that absence of the receptor was responsible for the severe disease called familial hypercholesterolemia (FH). Much earlier, in 1939, Carl Muller of the Oslo Community Hospital in Norway identified the disease as an inborn error of metabolism causing high blood cholesterol levels and heart attacks in young people; he recognized that it is transmitted as a dominant trait determined by a single gene. In the 1960's two forms of the disease were delineated, a heterozygous form and a more severe homozygous form. Heterozygotes, who inherit one mutant gene, are quite common about one in 500 people in most ethnic groups. Their plasma LDL level is twice the normal level (even before birth) and they begin to have heart attacks by the time they are 35; among people under 60 who have heart attacks, one in 20 has heterozygous FH.

If two FH heterozygotes marry (one in 250,000 marriages), each child has one chance in four of inheriting two copies of the mutant gene, one from each parent. Such FH homozygotes (about one in a million people) have a circulating LDL level more than six times higher than normal; heart attacks can occur at the age of two and are almost inevitable by the age of 20. It is notable that these children have none of the risk factors for atherosclerosis other than an elevated LDL level. They have normal blood pressure, do not smoke and do not have a high blood glucose level. Homozygous FH is a vivid experiment of nature. It demonstrates unequivocally the causal relation between an elevated circulating LDL level and atherosclerosis.

Heterozygotes with familial hypercholesterolemia can often be suspected at birth because blood plasma from the umbilical cord contains a two- to three-fold increase in the concentration of LDL-cholesterol. The elevated levels of plasma LDL persist throughout life, but symptoms typically do not develop until the third or fourth decade. The most important clinical feature is premature and accelerated coronary atherosclerosis. Myocardial infarctions begin to occur in affected men in the third decade, showing a peak incidence in the fourth and fifth decades. By age 60, approximately 85% have experienced a myocardial infarction. In women the incidence of myocardial infarction is also elevated, but the mean age of onset is delayed 10 years in comparison to men. Heterozygotes for familial hypercholesterolemia constitute about 5% of all patients who have a myocardial infarction.

Xanthomas of the tendons are the second major clinical manifestation of the heterozygous state. These xanthomas are nodular swellings that typically involve the Achilles and other tendons about the knee, elbow, and dorsum of the hand. They are formed by the deposition of LDL-derived cholesterol esters in tissue macrophages located in interstitial spaces. The macrophages are swollen with lipid droplets and form foal cells. Cholesterol is also deposited in the soft tissue of the eyelid, producing xanthelasma, and within the cornea, producing arcus lipoides corneae. Whereas tendon xanthomas are essentially diagnostic of familial hypercholesterolemia, xanthelasma and acrus lipoides corneae are not specific. The latter abnormalities also occur in many adults with normal plasma lipid levels. The incidence of tendon xanthomas in familial hypercholesterolemia increases with age. Eventually, about 75% of affected heterozygotes display this sign.

Homozygote individuals have marked elevations in the plasma level of LDL from birth. A unique type of planar cutaneous xanthoma is often present at birth and always develops within the last six years of life. These cutaneous xanthomas are raised, yellow plaque-like lesions that occur at points of cutaneous trauma, such as over the knees, elbows, and buttocks. Xanthomas are almost always present in the interdigital webs of the hands, particularly between the thumb and index finger. Tendon xanthomas, arcus lipoides corneae, and xanthelasma are also characteristic. Coronary artery atherosclerosis frequently has its clinical onset in homozygotes before age 10, and myocardial infarction has been reported as early as 18 months of age. In addition to coronary atherosclerosis, cholesterol is frequently deposited in the aortic valve, producing symptomatic aortic stenosis. Homozygotes usually succumb to the complications of myocardial infarction before age 30.

One in 500 persons in most populations has a mutation in the LDL receptor gene that destroys the function of the gene and produces the clinical syndrome of heterozygous familial hypercholesterolemia. Many of these mutant genes fail to produce any detectable receptors. Other mutant genes produce a small number of receptors; still other mutant genes produce essentially normal numbers of defective receptors that do not bind LDL properly. In other affected individuals, an LDL receptor protein of abnormal length is produced. Whereas the normal precursor form of the receptor displays an apparent molecular weight of approximately 120,000 daltons when measured by gel electrophoresis, aberrant forms of the protein encoded by mutant genes have been identified that migrate at apparent molecular weights of 100,000, 135,000 and 170,000 daltons. It is possible that such mutations observed in the LDL receptor protein may be the result of deletion or insertion mutations in the gene responsible for LDL receptor production. All of the above described mutations are felt to reside in or near the gene for the LDL receptor. Thus, a means of identifying directly those individuals who carry a mutant LDL receptor gene would greatly facilitate our ability to identify those individuals with a genetic predisposition towards developing atherosclerosis and heart disease. These mutations could be identified if a complementary DNA (cDNA) for the receptor gene were discovered.

BRIEF DESCRIPTION OF THE FIGURES

FIG. 3 (A-D) displays the nucleotide sequence of the cDNA corresponding to the human LDL receptor mRNA and the predicted amino acid sequence of the receptor protein. The nucleotides are numbered on the right-hand side in the 5'-to-3' direction; nucleotide 1 is the A of the ATG codon that encodes the initiator methionine; negative numbers refer to the 5' untranslated region. The amino acids are numbered underneath the sequence; residue 1 is the alanine found at the $NH_2$ terminus of the mature protein; negative numbers refer to the cleaved signal sequence. The signal sequence (21 residues) and the membrane-spanning sequence (22 residues) are indicated by single solid underlines. The sites to which N-linked carbohydrate could be attached (Asn-X-Ser or Asn-X-Thr) are indicated by double solid underlines. Cysteine residues are circled. A stretch of 48 residues rich in serines and threonines to which O-linked carbohydrate could be attached is indicated by the dotted underlines. The Alu sequences in the 3' untranslated region of the cDNA are boxed; the direct repeats associated with the first Alu sequence are indicated by dotted arrows above the sequence. Three potential polyadenylation signals in the 3' untranslated region are indicated by overlines and underlines.

FIG. 4 is an analysis of Xba I restriction digests of genomic DNA from a normal subject and an individual with familial hypercholesterolemia (designated FH274) with DNA probes from different regions of the LDL receptor cDNA.

SUMMARY OF THE INVENTION

Figure 1:
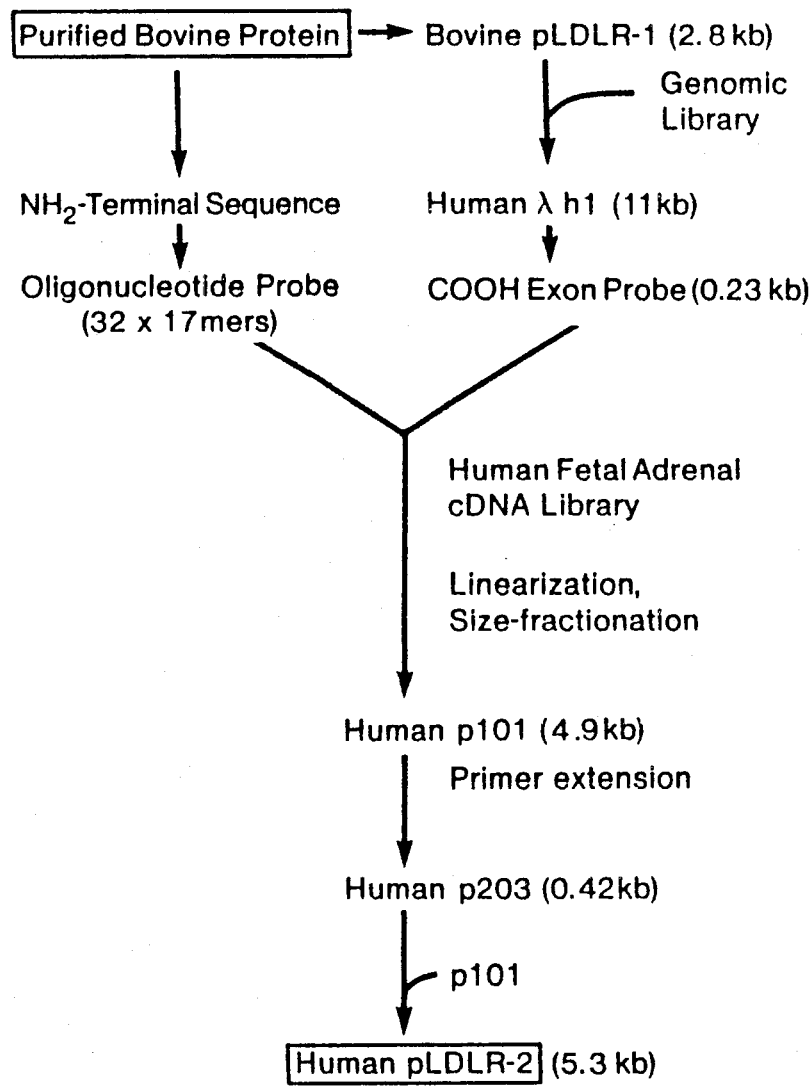
FIG. 1 is a schematic representation of the cDNA cloning strategy used in cloning the human LDL receptor. Human λh1 is a partial genomic clone corresponding to the 3' end of the LDL receptor gene. Recombinant plasmids p101 and p203 contain partial cDNA's which are complementary to the human LDL receptor mRNA. Plasmid pLDLR-2 is a fusion construct of p101 and p203 and contains a nearly full-length cDNA for the human LDL receptor mRNA. The numbers in parentheses refer to the lengths of the DNA inserts in a given clone.

The present invention discloses a technique suitable for the construction of recombinant DNA transfer vectors which contain a cDNA sequence corresponding to the mRNA sequence of the human Low Density Lipoprotein (LDL) receptor gene. In addition, the present invention discloses recombinant DNA transfer vectors that contain DNA inserts which are complementary to various portions of either the human LDL receptor gene or the mRNA transcript of that gene.

Recombinant DNA transfer vectors disclosed by the present invention need not necessarily contain the entire human LDL receptor gene in order to be useful in the practice of the invention. Similarly, the recombinant transfer vector need not contain a DNA fragment which is complementary to the entire mRNA transcript for that gene. Recombinant transfer vectors may be constructed of smaller subfragments which are complementary to either the human LDL receptor gene or the mRNA for that gene. In fact, the use of different subfragments of the gene as probes may be necessary for detailing specific mutations in certain FH individuals. All that is required is that these fragments be of sufficient length to form a stable duplex or hybrid. Such fragments are said to be "hybridizable" in that they are capable of stable duplex formation. Generally, DNA fragments at least fourteen nucleotides in length are capable of forming stable duplex's (i.e.—a tetradecamer).

Individuals with Familial Hypercholesterolemia (FH) are diagnosed using the present invention by determining the presence of a mutation in the gene which codes for the LDL receptor. DNA isolated from the recombinant cDNA clones has been used to diagnose one patient with familial hypercholesterolemia who has a deletion in the gene. The cDNA, or fragments thereof, should also be useful in diagnosing other mutations, including those resulting from single nucleotide changes (point mutations).

In general, the method consists of fragmenting the DNA from cells of an individual who is suspected of having a mutation followed by separating the DNA fragments into a pattern according to some physiochemical property of the DNA, for example, molecular weight or size of the DNA fragments. The separated DNA is then hybridization probed with labeled LDL receptor DNA in order to identify those fragments of DNA from the individual which correspond to the LDL receptor gene. Then, by comparing the pattern of LDL receptor gene fragments of the suspected individual to a similar fragment pattern from a normal individual, it can be determined whether the suspected individual displays a mutation. If the pattern of LDL receptor gene fragments identified in the suspected individual exhibits an alteration relative to the control pattern, a gene mutation has been detected.

One method which has proved particularly useful in fragmenting the DNA utilizes restriction enzyme digestion. However, other methods, including chemical cleavage of the DNA, could also be used providing that such methods are capable of reproducibly cleaving genomic DNA into the same discrete fragments.

The fragmented DNA can be separated into a recognizable pattern using various methods, the most useful of which take advantage of the varying sizes of the discrete DNA. For example, DNA fragments can be separated according to molecular weight by velocity sedimentation through a density gradient, or, by molecular size by gel exclusion chromatography. However, for the purposes of the present invention, the preferred technique is to separate the DNA fragments by electrophoresis through an agarose or polyacrylamide gel matrix.

The cloned LDL receptor DNA can be conveniently labeled with radioactive nucleides which allow for ready visualization of the corresponding genomic LDL receptor DNA fragment pattern after hybridization and autoradiography. Other labeling techniques, including for example, heavy isotopes, would be possible but would prove cumbersome in practice as a means of identifying the corresponding genomic sequences.

In addition to the use of cloned DNA fragments diagnosis can in principle be made with chemically synthesized oligonucleotides that correspond to portions of the cDNA that are disclosed herein. Genomic DNA from individuals with single base substitutions in the LDL receptor gene will hybridize to such oligonucleotides less strongly than does DNA from a normal individual. Such weakened hybridization will therefore be a method of diagnosis of many patients with FH in both the heterozygous and homozygous forms.

DETAILED DESCRIPTION OF THE PREFERRED EMBODIMENTS

The low density lipoprotein (LDL) receptor is a cell surface protein that plays a central role in the metabolism of cholesterol in humans and animals. Through the process of endocytosis, the LDL receptor is responsible for binding serum cholesterol and making it available for cellular metabolism. This is made possible by internalization of the receptor/cholesterol complex, the cholesterol then being liberated by catabolism of the internalized complex. The liberated cholesterol regulates, via a feedback mechanism, the rate of synthesis of the LDL receptor. The increased demand for cholesterol in certain steroidogenic tissues, such as the adrenal cortex and the ovarian corpus luteum, is met by an increased number of LDL receptors. A foremost distinguishing feature of the LDL receptor is that mutations affecting its structure and function give rise to one of the most prevalent human genetic diseases, familial hypercholesterolemia.

Recombinant DNA technology provides one approach to detecting the presence of mutations in an individual suspected of having FH. By using a probe consisting of a purified human LDL receptor gene, or a hybridizable subfragment thereof, abnormalities present in a particular individual's LDL receptor gene can be identified and that individual can then be targeted for other types of therapy aimed at addressing the symptoms of FH. That is, once FH individuals are identified through processes disclosed by the present invention, these individuals can be targeted for therapy, including both diet modification, pharmacologic approaches, and surgery, all aimed at reducing the levels of circulating cholesterol in these individuals. In addition, knowledge concerning the genetic structure of the LDL receptor gene in FH individuals could eventually lead to more dramatic therapeutic approaches to the disease, including somatic gene replacement or modification.

The first step in understanding and identifying the underlying genetic abnormalities in FH individuals is through the development of suitable probes, using genetic engineering techniques, by which both normal and abnormal LDL receptor genes may be studied. The most ideal genetic probe for studying the structure of the human LDL receptor gene would be a cloned human LDL receptor gene or a cDNA prepared to the receptor mRNA. However, there are difficulties in approaching this problem directly in that it would require isolation of the probe from some human source. This source would preferably be an adrenal or ovarian source where the receptor, and its mRNA, are in greater abundance. This approach is somewhat impractical in that it is difficult to obtain sufficient amounts of the appropriate human tissues. The present invention describes a fortuitous approach whereby the LDL receptor cDNA is cloned from a bovine source and the cloned bovine LDL receptor cDNA is then used to isolate part of the human gene from a gene library. The part of the human gene is then used to isolate nearly full-length human cDNA clones. This was fortuitous in that it was not apparent until after the human cDNA was cloned and sequenced, that the bovine sequences which were used as hybridization probes could be used to correctly probe for the human LDL receptor gene. In retrospect, the homology between the bovine and human gene was sufficient enough to allow for the cloning approach detailed herein.

The isolation of human recombinant DNA clones, bearing copies of the human LDL receptor mRNA, facilitated the development of an assay whereby LDL receptor gene mutations could be detected. To illustrate the utility of this assay, a case study of an individual afflicted with familial hypercholesterolemia (hereinafter designated FH 274) was undertaken. Although the case study described herein goes into extreme detail as to the structure of that individuals specific genetic defect, it is not contemplated by the present invention that such measures will be necessary as a diagnostic approach. However, this material is included herein to illustrate the power of these genetic techniques which are made available by the present invention. Moreover, they provide a means whereby many other defects in the LDL receptor gene may be diagnosed.

Thus, the present invention provides a method whereby not only may the presence of a genetic defect in the LDL receptor gene be identified but, in addition, the particular genetic defect may be detailed with great specification.

The present inventors feel that these techniques provide a method whereby segments of the population as a whole may be screened for the presence of genetic defects in the LDL receptor gene. Once these individuals are identified through the screening procedures detailed herein, the specific abnormalities exhibited by the mutant LDL receptor gene can then be studied in great detail. Therefore, the present Applicants feel that the present invention will lead to a greater future understanding of the genetic events which give rise to the serious and prevalent human genetic disease, Familial Hypercholesterolemia.

EXAMPLE I

CLONING OF THE BOVINE LDL RECEPTOR GENE cDNA

A Bovine LDL receptor gene cDNA clone, hereinafter designated pLDLR-1, was isolated using a combination of polysome immunopurification and oligonucleotide hybridization. Generally, the technique proceeds through five steps. These steps consist of (1) isolation of the bovine receptor protein, (2) generation of a polyclonal antibody capable of reacting with the bovine LDL receptor protein, (3) specific immunoprecipitation of those bovine polysomes which are actively engaged in translation of the bovine receptor mRNA, followed by enriching for the receptor mRNA isolated from the precipitated polysomes, (4) preparation of a cDNA clone bank from the enriched mRNA, (5) screening of the cDNA clone bank to isolate a representative clone bearing a bovine LDL receptor cDNA insert. These steps are described in detail as follows.

Bovine Receptor Isolation and Generation of a Polyclonal Antibody

Homogeneous LDL receptor protein was isolated from bovine adrenal cortex as described by Schneider, et al., *J. Biol. Chem.*, 257:2664–2673 (1982), incorporated herein by reference. A polyclonal antibody against the bovine adrenal LDL receptor was raised in rabbits and purified on staphylococcal protein A-sepharose as described by Tolleshaug, et al. *Cell*, 30:715–724 (1982), incorporated herein by reference. This antibody and its corresponding non-immune rabbit IgG were free of gross RNase contamination as shown by their failure to alter the sedimentation behavior of polysomes or sucrose gradients.

Polysome Immunoprecipitation of Bovine LDL Receptor mRNA

Polysomes enriched in mRNA for the LDL receptor were prepared as follows. Bovine tissue was frozen in liquid nitrogen within 5 min of slaughter. Adrenal glands were powdered in liquid nitrogen in a Waring blender and stored at −70° C. prior to polysome isolation.

Ten-gram aliquots of powdered adrenals were homogenized with a Brinkmann Polytron in 42 ml of 25 mM Tris-HCl, pH 7.5/25 mM NaCl/5 mM MgCl$_2$/2% (vol/vol) Triton X-100/0.3 mg of heparin per ml/1 µg of trichodermin per ml/60 µg of phenylmethylsulfonyl fluoride per ml. Polysomes were isolated from the homogenate by MgCl$_2$ precipitation as described by Palmiter, *Biochemistry*, 13:3606–3615 (1974) (incorporated herein by reference), and stored at −70°. Twenty-five A$_{260}$ units of polysomes were obtained per gram of adrenal powder.

On linear sucrose gradients approximately 70% of the A$_{260}$ material sedimented as polysomes; the remaining absorbance was present in 80S monosomes. Polysomes (1,000 A$_{260}$ units) were clarified with a 10 minute centrifugation at 20,000×g, then diluted to 15 A$_{260}$/ml in a buffer containing 25 mM Tris-HCl at pH 7.5, 150 mM NaCl, 5 mM MgCl$_2$ 0.1% Nonidet P-40, heparin at 0.2 mg/ml, and trichodermin at 1 µg/ml and incubated with 6.25 mg of anti-receptor IgG or non-immune IgG for 1 hour with stirring at 4° C.

The polysome/antibody slurry was then passed twice through a column of protein A-Sepharose (0.7×13 cm) equilibrated in the above dilution buffer at a flow rate of 8–10 ml/hour at 4° C. The column was washed overnight with 120 ml of dilution buffer. Bound polysomes were eluted at a maximal flow rate with 20 ml of 25 mM Tris-HCl, pH 7.5/20 mM EDTA. The eluted fraction was heated 5 minutes at 65° C., brought to 0.5M NaCl and 0.2% NaDodSO$_4$ cooled to 24° C., and passed through a column of oligo(dT)-cellulose (0.8×2.3 cm) equilibrated in 10 mM Tris HCl, pH 7.5/0.5M NaCl. The column was washed with 20 ml of this buffer and poly(A)+ RNA was eluted with 5 ml of 10 mM Tris-HCl, pH 7.5. Yeast carrier tRNA (50 µg) was added, and the RNA was precipitated twice with NaOAc and ethanol. This immunopurified poly(A)+ RNA was resuspended in 20 µl of water and stored at −70° C.

The immunoselected poly(A)+ RNA was assayed for the presence of LDL receptor mRNA by in vitro translation in a reticulocyte lysate system. The lysate system is described as follows.

Aliquots of poly(A)+ mRNA were incubated with 2.5 mM CH$_3$HgOH for 10 min at 4° C. and then translated in rabbit reticulocyte lysates prepared as described by Pelham and Jackson, *Eur. J. Biochem.*, 67:247–256 (1970), and supplemented with 80 mM KOAc, 1 mM Mg(OAc)$_2$, 19 amino acids (excluding methionine) at 16 µM each, and [$^{35}$S]methionine at 0.2 mCi/ml (1 Ci=3.7×10$^{10}$Bq). The final concentration of CH$_3$HgOH in the translation reaction was 0.3 mM. Translation products were analyzed by electrophoresis on NaDodSO$_4$/7% polyacrylamide gels.

Total adrenal gland poly(A)+ RNA directed the synthesis of many proteins, as determined by NaDodSO$_4$ gel electrophoresis and fluorography of the synthesized products. Poly(A)+ RNA derived from the immunopurified polysomes directed synthesis of several of the same protein bands plus one clear addition: a protein that migrated with a M$_r$ of approximately 120,000. This protein was not demonstrable after translation of poly(A)+ RNA selected from polysomes with nonimmune IgG. Biosynthetic studies on the LDL receptor from hamsters and rabbits have shown that the receptor is initially made as an apparent 120,000 M$_r$ precursor (where M$_r$ stands for molecular weight in daltons) that undergoes a series of posttranslational glycosylation events during transport to the cell surface, resulting in a mature protein with an apparent M$_r$ of 60,000. Thus, the size of the enriched protein seen after translation of the immunoselected poly(A)+ RNA was consistent with that of the LDL receptor precursor.

Preparation and Screening of the Bovine cDNA Clone Bank

The immunoselected poly(A)+ RNA was used to construct a cDNA library by the method of Okayama and Berg, *Mol. Cell. Biol.*, 2:161-170 (1982) (incorporated herein by reference) from poly(A)+ RNA derived from 2,000 A$_{260}$ units of polysomes. In the cloning reactions, which employed enzymes obtained from Life Sciences and P-L Biochemicals, 1.4 µg of dT-tailed vector primer and 0.52 pmol of dG-tailed linker were used.

Portions of the cDNA library were used to transform *Escherichia coli* RR1 to ampicillin resistance by the CaCl$_2$-shock procedure described in Maniatis, et al. *Molecular Cloning* (Cold Springs Harbor Laboratory, Cold Spring Harbor, N.Y., page 250), incorporated herein by reference. Colonies were plated at high density on nitrocellulose filters, and two replica filters were prepared for hybridization (Maniatis, supra. p. 316). To reduce nonspecific background, baked filters were washed overnight in 50 mM Tris-HCL, pH 8/1 mM EDTA/1M NaCl/0.1% NaDodSO$_4$ at 37° or 42° C. and then incubated at 65° C. for 3 hr in 4 x SSC (1 x SSC=0.15M NaCl/15 mM sodium citrate), 10 X Denhardt's solution (1X=0.02% polyvinylpyrrolidine/0.02% bovine serum albumin/0.02% Ficoll) (Maniatis, supra, p. 327), and sonicated and denatured *E. coli* DNA at 1000 µg/ml.

Hybridization was performed overnight in the latter solution containing $^{32}$P-5′-end-labeled oligonucleotide mixtures (6×10$^6$ cpm/pmol at 1 pmol/ml) prepared as described below. Hybridization temperature for a given oligonucleotide probe corresponded to the minimum melting temperature, t$_m$, calculated from the empirical formula t$_m$=2° C.×(number of dA dT bp)+4° C.×(number of dG dC bp), in which bp is base pairs. Filters were washed three times in 4×SSC at the hybridization temperature for 30 minutes per wash, dried at room temperature, and subjected to autoradiography. Positive clones were picked from the master plate and purified through several rounds of screening.

The hybridization probes used in the screening protocol detailed above were prepared based on sequence information obtained from peptide subfragments of the LDL receptor protein as follows.

The purified LDL receptor was digested with CNBr, an internal CNBr fragment was isolated by high pressure liquid chromatography (HPLC), and its partial amino acid sequence was determined by automated Edman degradation. CNBr fragments were generated from two different preparations of reduced and [$^3$H] carboxymethylated receptor (1.6 and 1.8 mg of protein)

and fractionated by reverse-phase HPLC on a Brownlee (Santa Clara, Calif.) RP 300 column. The CNBr peptide described here was subjected to two separate runs on an automated Beckman 890C sequencer using a 0.25M Quadrol program and the nonprotein carrier Polybrene. Yields of the $NH_2$-terminal residue of the CNBr peptide were 400 and 1,100 pmol for the two runs. Repetitive yields, calculated on the basis of recovery of the phenylthiolhydantion of [$^3$H] cysteine, averaged 91%.

Two families of synthetic oligonucleotide probes that corresponded to all possible codons specifying the sequence of amino acids in two neighboring regions of this CNBr fragment were synthesized. One family of oligonucleotides, designated A in Table I consisted of 32 tetradecamers encoding (Met)-Ala-Glu-Asn-Leu. The existence of a methionine residue at the amino terminus of this sequence was inferred from the fact that the peptide was generated by CNBr digestion. A second family of tetradecames, designated B and B* in Table I, encoded the sequence Pro-Glu-(Asp)-Ile-Val. The assignment of the Asp residue in this sequence was provisional because it was observed in only one of two sequenator runs. The B/B* oligonucleotide family consisted of a total of 48 members that were synthesized as two subfamilies of 24 each, differing only in the codons used to specify the Pro residue ($CC_T{^C}$ in B and $CC_G{^A}$ in B*).

TABLE I

CNBr Peptide Sequence and Oligonucleotide Synthesis

Met Ala Glu Asn Leu Leu Ser Pro Glu (Asp) Ile Val

```
         C                       C       C
    T A  C C                T  A C       T
ATGGC GA AA   T          CC GA GA AT    GT
    A  G T T                A  G T      A
    G                       G
```

| Oligo Family A | Oligo Families B and B* |
|---|---|
| 32 × 14 mers | 2 × 24 × 14 mers |

Thirty hybridization positive cDNA clones were identified by screening the above cDNA library with oligonucleotide family B. When these clones were probed separately with the subfamilies B or B*, 16 clones hybridized strongly with oligonucleotide mixture B, but not with B*. Twelve of the 30 clones were positive only with mixture B*. These 28 positive clones were then screened with oligonucleotide mixture A, and two plasmids, both from the latter group of 12, hybridized with this probe. These two clones were considered to contain cDNAs for the receptor and were chosen for further study.

Plasmid DNAs from the two clones that hybridized to both the B* and A oligonucleotide probes were subjected to restriction endonuclease mapping, and the results indicated that these two clones were identical. Therefore, these clones were considered to be representative bovine LDL receptor cDNA clones. One of these clones, designated pLDLR-1, was chosen in order to confirm that it represented a true LDL receptor clone.

To confirm the identity of pLDLR-1, total poly(A)+ RNA was extracted from bovine adrenal glands and liver and analyzed in blotting experiments using nick-translated $^{32}$P-labeled plasmid as a probe. RNA blotting experiments were performed as follows. Total RNA was isolated by treatment of tissues or cells with guanidinium thiocyanate (Maniatis, supra, page 196). Poly(A)+ RNA was purified by oligo(dT)-cellulose chromatography, denatured with glyoxal, size-fractionated by electrophoresis (20 volts for 16 hours) on 1.5% agarose gels containing 40 mM 3-N-morpholino-propanesulfonic acid (pH 7.0), and then transferred to Zeta Probe membranes (Bio-Rad) by capillary blotting in 20×SSC. Prehybridization and hybridization were carried out as described by Maniatis, supra, page 320.

Increasing amounts of adrenal gland RNA yielded a progressively stronger hybridization signal corresponding to a mRNA of approximately 5.5 kb. Densitometric scanning showed that the signal obtained with a given amount of adrenal RNA was 9-fold more intense than that obtained with the same amount of liver RNA. Previous studies have shown that functional LDL receptor activity is about one order of magnitude more abundant in bovine adrenal than in bovine liver, a finding that coincides with the difference in the abundance of the mRNAs discussed above.

The number of LDL receptors can be markedly reduced when cultured cells are grown in the presence of cholesterol or related sterols. Poly(A)+ RNA was isolated from human A-431 cells grown in the absence of sterols (receptor-induced) and presence of sterols (receptor-suppressed) and analyzed by blotting with pLDLR-1. A strong hybridization signal from a mRNA of approximately 5.5 kb was detected in the induced RNA and this signal was reduced by more than 90% in the suppressed RNA.

These results indicate that pLDLR-1 contains a cDNA copy of at least a portion of the bovine LDL receptor gene. This clone has been deposited as ATCC #39965. Fortunately, there is sufficient homology between the bovine receptor gene and the human gene to allow the use of the bovine sequence as a probe in isolating the human gene. These procedures are disclosed in Example II.

EXAMPLE II

Cloning and Characterization of the Human LDL Receptor Gene

The strategy used to obtain a full-length cDNA for the human LDL receptor is outlined in FIG. 1. The partial bovine cDNA (pLDLR-1) was used to screen a human genomic library cloned in bacteriophage λ by the procedure of Lawn, et al., Cell, 15:1157–1174 (1978) (incorporated by reference herein) as follows. Approximately $1 \times 10^6$ bacteriophages containing human genomic DNA inserts were screened with $^{32}$P-labeled pLDLR-1. Hybridization was performed under conditions of reduced stringency: 30% formamide, 5×SSC, 5×Denhardt's solution, 0.1% SDS (Sodium Dodecyl Sulfate), 100 μg/ml salmon sperm DNA and 1 μg/ml poly(A) at 42° C. Filters were washed twice at 22° C. for 10 minutes in 2×SSC, 0.1% SDS (sodium dodecyl sulfate), and once at 54° C. for 60 minutes in the same solution.

From this human genomic clone library, a single clone, λh1, was identified. It contained an 11 kb (kilobase pair) insert encoding the 3' end of the human LDL receptor gene. λh1 was used to generate a 236 bp Pvu II fragment that served as a unique probe for the COOH-terminal end of the human LDL receptor cDNA.

A cDNA library was constructed from human fetal adrenal poly(A)+ RNA by the method of Okayama and Berg, *Mol. Cell. Biol.*, 2:161–170 (1982), incorporated herein by reference. In the cloning reactions, we used commercially obtained enzymes, 2 μg of poly (A)+ RNA, 1.5 μg of dT-tailed pcDV1vector-primer, and 0.52 pmole of dG-tailed linker. Following transformation into *E. coli* HB101, plasmid cDNAs were isolated from approximately $3 \times 10^5$ transformants and enriched for longer cDNAs (6 to 10 kb) by the sublibrary method of Okayama and Berg, *Mol. Cell. Biol.*, 3:280–289 (1983) incorporated herein by reference.

Human LDL receptor cDNAs were identified using two probes, a 5'-specific oligonucleotide family consisting of 32 heptadecamers derived from the sequence Asn-Glu-Phe-Glu-Cys-Gln, present at the $NH_2$ terminus of the bovine LDL receptor protein and the 3'-specific 236 base pair Pvu II fragment containing a 158 bp COOH-terminal exon that was derived from the human genomic clone λh1(described above). Oligonucleotides were synthesized by the phosphoramidite method and provided by Mark Zoller (Cold Spring Harbor Laboratory) and Ray MacDonald (University of Texas Health Science Center at Dallas). Replica filters were screened, and five colonies out of 2396 recombinants were positive with both the 5'- and 3'-specific probes. The plasmid with the longest cDNA insert in these positive clones (4.9 kb) was designated p101.

The nucleotide sequence of the cDNA insert of p101 revealed that it did not contain the 5'end of the coding region of the LDL receptor mRNA. Nucleotide sequence analysis of this cDNA revealed that the 5'-oligonucleotide probe was not hybridizing to the region corresponding to the extreme $NH_2$ terminus of the protein. Rather, the probe was hybridizing to an imperfect repeat of the $NH_2$-terminal sequence that occurred within the coding region. The open reading frame continued to the extreme 5' end of the cDNA insert in p101, and there was no evidence of a predicted signal sequence or an initiator methionine codon. Therefore, p101 did not contain the entire coding region.

To obtain the rest of the coding region, an oligonucleotide corresponding to a sequence near the 5' end of the cDNA insert in p101 was prepared and primer extension using human fetal adrenal poly(A)+ RNA as a template was performed. A synthetic oligonucleotide of 20 bases complementary to the mRNA strand and originating 63 nucleotides from the 5' end of the cDNA insert of p101 was used to construct a primer-extended cDNA library from human fetal adrenal poly(A)+ RNA in pBR322. This library was screened with a second oligonucleotide of 20 bases that originated 8 nucleotides from the 5' end of the cDNA insert of p101. Of the 1044 recombinants screened, one plasmid, designated p203, was identified whose cDNA insert overlapped that of p101 for 83 nucleotides and extended to near the approximate 5' end of the human LDL receptor mRNA.

Figure 2:
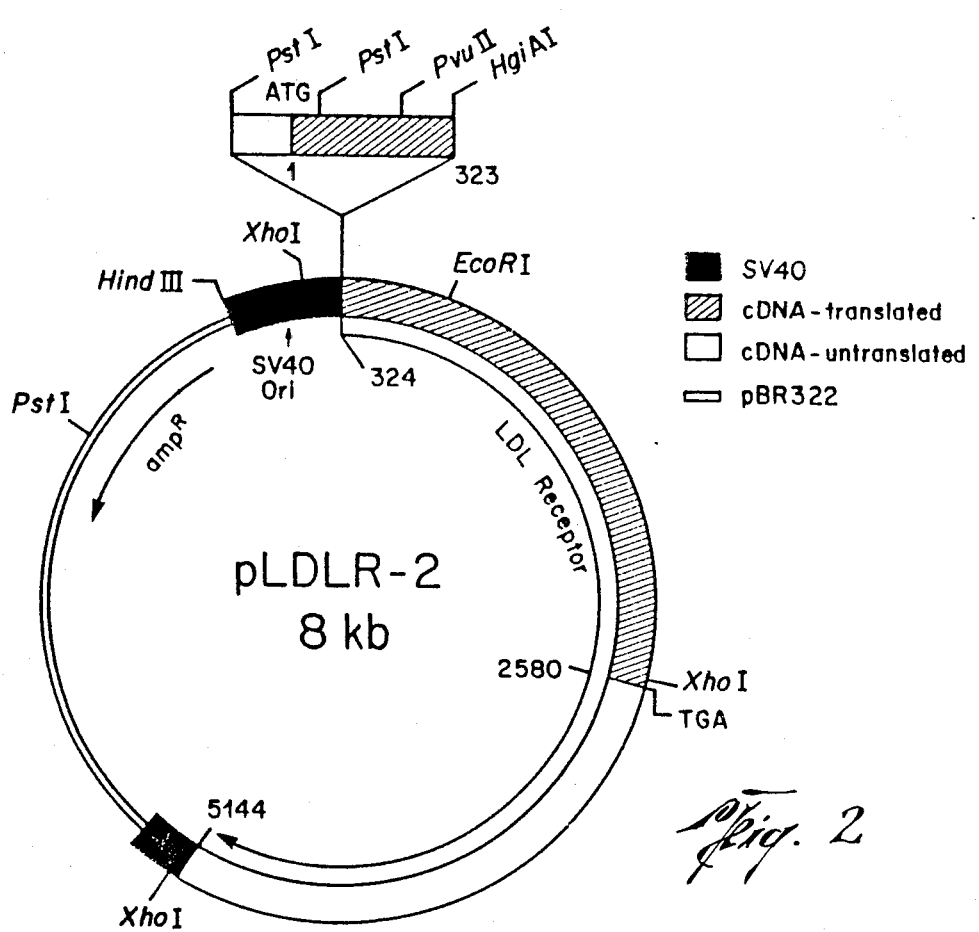
FIG. 2 is a structural representation of recombinant plasmid pLDLR-2 which contains a nearly full-length cDNA for the human LDL receptor gene. The coding region (hatched area) encompasses nucleotides 1 to 2580. This fusion plasmid was constructed by joining the cDNA inserts of p203 (nucleotides 1 to 323) and p101 (nucleotides 324 to 5144) via overlapping Hgi A1 sites. The solid areas in pLDLR-2 denote regions in the cloning vector that contain SV40 sequences, including the origin of replication, 16S and 19S donor and acceptor splicing sites, and polyadenylation signals.

To construct a nearly full-length cDNA, it was necessary to ligate the appropriate portions of p101 and p203 (FIG. 2). Owing to a paucity of convenient restriction enzyme sites, this ligation required several partial digests and the preparation of two intermediate plasmids as follows.

A cDNA containing the entire translated region of the human LDL receptor mRNA, was constructed by joining the ineserts of p203 and p101 via overlapping Hgi A1 sites (FIG. 2). The construction involved three partial digestions, three multifragment ligations, and two intermediate plasmids. p203 was partially digested with Pst 1 and then digested completely with Pvu II to yield a fragment of 341 bp. A Hind III-Pst 1 (518 bp) fragment was purified from pL 1, which contains the early region promoter and splicing signals of the SV40 virus (see FIG. 2 and Okayama and Berg, 1983). These two fragments were ligated and cloned into the Hind III-Pvu II site of pBR322. This intermediate plasmid was designated pHP1. A 394 bp Hgi AI-Eco R1 fragment from the 5' end of p101 was mixed with a 105 bp Pvu II-Hgi A1 fragment from the 3' end of p203 and ligated into Eco R1-Pvu II-digested pBR322. This intermediate plasmid was designated pEP1. pEP1 was partially digested with Pvu II and then completely digested with Eco R1 to yield a 499 bp Pvu II-Eco R1 fragment. This DNA fragment was ligated with the 859 bp Hind III-Pvu II insert from pHP1 and with the 7 kb Hind III-Eco R1 fragment of p101 corresponding to the 3' eighty-five percent of the cDNA and the cloning vector. The final 8.4 kb plasmid designated pLDLR-2, contained a full-length cDNA copy of the human LDL receptor linked to SV40 sequences (FIG. 2).

The result of this genetic engineering was pLDLR-2, a plasmid containing a 5.3 kb cDNA insert corresponding to the entire coding region, the entire 3' untranslated region, and at least a portion of the 5' untranslated region of the human LDL receptor mRNA (ATCC #39966).

The cDNA insert of pLDLR-2 was sequenced by the method of Maxam and Gilbert, *Meth. Enzymol.*, 65:499–500 (1980)and Sanger et al, *Proc. Natl. Acad. Sci. U.S.A.*, 74: 5463–5467 (1977), both of which are incorporated herein by reference. The nucleotide sequence determined for the human LDL receptor cDNA is displayed in FIG. 3 along with the predicted amino acid sequence of the corresponding receptor protein. On the 5' side of the 5' end of the sequence shown in FIG. 3, plasmid pLDLR-2 contains extraneous DNA that appeared to arise from the formation of a hairpin loop during the cloning reactions. The presence of this extraneous DNA in no way affects the utility of this cDNA for the diagnostic purposes outlined in this application.

EXAMPLE III

ISOLATION OF GENOMIC RECOMBINANT CLONES CORRESPONDING TO THE NORMAL LDL RECEPTOR GENE

Genomic clones spanning the 3' end of the human LDL receptor gene were isolated from a genomic library constructed in the bacteriophage vector, λCharon 4A. The library was provided us by T. Maniatis, Harvard University. Recombinant phage were screened with $^{32}P$-labeled pLDLR-1 and pLDLR-2, cDNA probes for the bovine and human LDL receptors (see Examples I and II, respectively). Hybridization was performed under stringent conditions: 50% formamide, 5×SSPE (1×SSPE=0.18M NaCl/10 mM $NaH_2PO_4$, pH 7.4/2 mM EDTA), 5×Denhardt's solution , 0.1% SDS, 100 μg/ml salmon sperm DNA, and 1 μg/ml poly(A) at 42° for 16 hours. Filters were washed twice at 22° C. for 10 minutes in 2×SSC (1×SSC=0.15M NaCl/0.015M sodium citrate), 0.1% SDS and once at 60° C. for greater than or equal to 2 hours in 0.1×SSC and 0.1% SDS. Washed filters were air-dried and subjected to autoradiography at −70° C. with Kodak XAR-5 film and Dupont Cronex Lighting Plus Intensifying screens.

Figure 6:
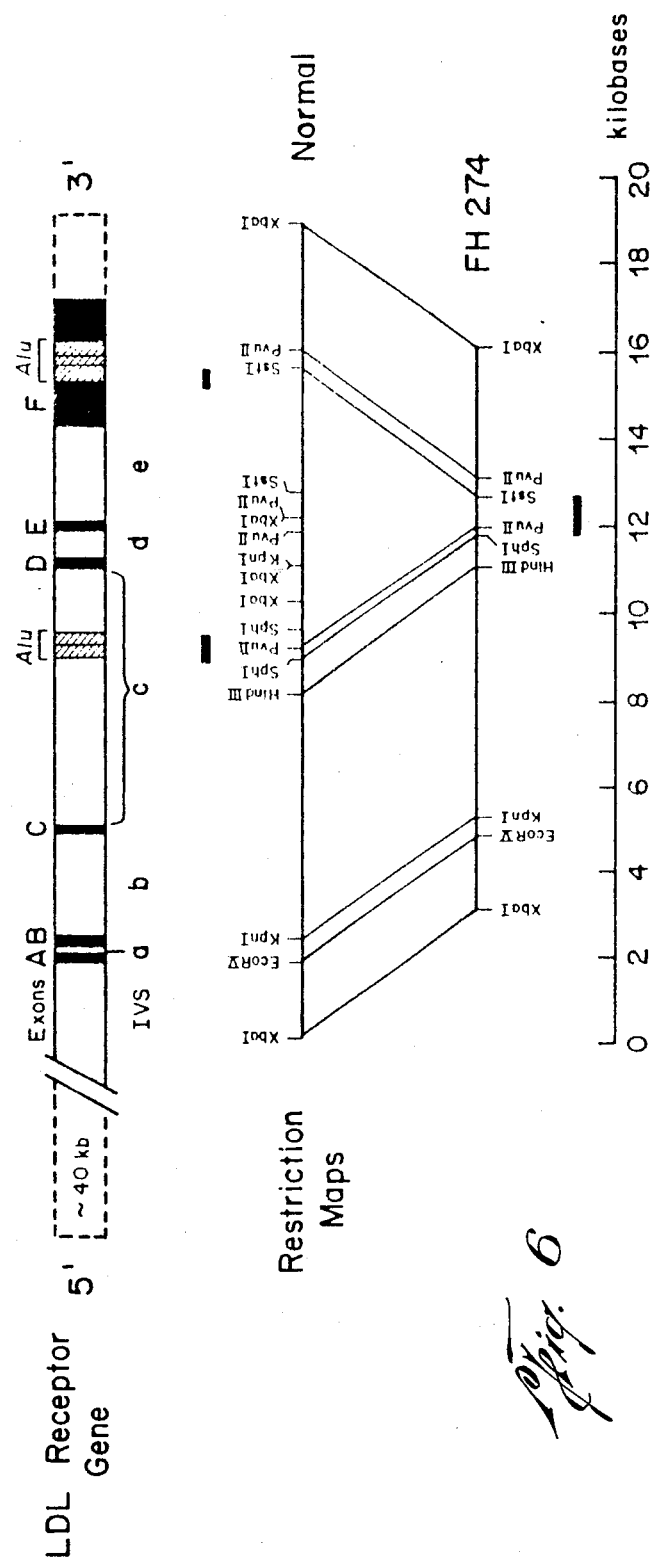
FIG. 6 is a comparison of restriction maps of the 3' end of the normal LDL receptor gene and the deletion-bearing gene from FH 274. The scale at the bottom indicates the length of genomic DNA in kilobases. The organization of the normal LDL receptor gene is shown in the diagram at the top. Exons are indicated by solid segments and upper case letters; intervening sequences (IVS) are indicated by open segments and lower case letters. The Alu repetitive sequences in IVS c and Exon F are indicated. Restriction enzyme recognition sites used to define the gene deletion in FH 274 are shown.

The 3' end of the normal LDL receptor gene shown in FIG. 6 is contained on three of the λclones isolated in the above manner: λ33-2, λ33-1, and λh1 (obtainable from ATCC deposit numbers 40148, 40147 and 40149, respectively). Note that the restriction map of the normal LDL receptor gene shown in FIG. 6 also displays both "exons" and IVS regions (intervening sequences or "introns"). The term "exons" refers to domains of a gene that are "transcribed" into mRNA and eventually appear in the cytoplasm as mature mRNA. Any one gene may have numerous exons, which together, comprise the structural gene itself. Exons are separated within the gene by regions referred to as "intervening sequences" or IVS regions. The IVS regions are transcribed into the initial RNA transcript of the DNA. However, unlike exons, the IVS regions are processed out of the initial RNA transcript and are therefore never expressed in the ultimate protein product.

The DNA insert in λ33-2, approximately 12 kb, encodes Exons A, B, and C; the insert in λ33-1, approximately 11 kb, encodes Exons D, E, and F; and the insert in λh1, approximately 11 kb, encodes Exons E and F. The $^{32}$P-cDNA probes shown in FIG. 4A correspond to the following regions of the LDL receptor gene: probes 2-5 hybridize to exons in the 5' end of the LDL receptor gene denoted as approximately 40 kb of DNA in FIG. 6; probe 6 hybridizes to Exon C; probe 7 hybridizes to the 5' half of Exon F; and probes 8 and 9 both hybridize to the 3' half of Exon F. Exon C encodes the O-linked sugar region of the receptor (amino acid residues 693 to 749); Exon D encodes the region between the O-linked sugar domain and the membrane-spanning domain plus 8 of the 22 amino acids comprising the membrane-spanning domain (residues 750 to 775); Exon E encodes the remainder of the membrane-spanning domain and 39 of the 50 amino acids comprising the cytoplasmic domain (residues 776 to 828); Exon F encodes the terminal 11 amino acids of the cytoplasmic domain of the receptor protein residues 829 to 839) plus all of the 3' untranslated region of the mRNA.

EXAMPLE IV

CASE STUDY OF AN INDIVIDUAL WITH FAMILIAL HYPERCHOLESTEROLEMIA

The present example discloses the use of the recombinant clones disclosed in Example's II and III to characterize a mutation in the structural gene for the LDL receptor in a family with FH. The index case is a young man (B.H.), hereafter designated FH 274, who has all of the clinical features of homozygous FH. Previous functional studies revealed that cultured fibroblasts from FH 274 bound about one-third of the normal amount of $^{125}$I-labeled LDL. However, the receptors in FH 274 did not cluster in coated pits and hence did not transport their bound LDL into the cell. Thus, FH 274 was categorized functionally as an "internalization-defective" mutation. Studies of fibroblasts from the relatives of FH 274 revealed that he had inherited two different mutant alleles; the allele encoding the internalization-defective receptor was inherited from his mother and a null (or silent) allele that produced no functional receptor protein was inherited from his father.

Preliminary biosynthetic studies of cultured fibroblasts from FH 274 revealed that the LDL receptor protein encoded by the internalization-defective allele is about 10,000 daltons smaller than the normal receptor. Accordingly, a study of this mutation was initiated by analyzing the genomic DNA from FH 274 and his family members. As described below, we found that the mutant gene has undergone a large deletion that eliminates two exons completely and one exon partially.

The deletion mutation revealed by practice of the present invention with respect to FH 274 was shown to result from a recombination between two repetitive DNA elements: an Alu element in the intervening sequence (IVS) that precedes the exon encoding the membrane-spanning region of the receptor and an Alu element in the exon encoding the 3'-untranslated region of the gene. Alu sequences are human DNA sequences which display a highly repetitive character. It is thought that due to their highly repetitive nature, Alu sequences may be responsible for a number of genetic mutations: an Alu sequence from one region of a gene may cross-hybridize with Alu sequences from another region, forming a "loop" in the DNA. Thus, the deletion occurs when this "loop" is processed out of the gene, leaving an incomplete gene.

The resulting mutant gene, in the case of FH 274, produces a truncated LDL receptor that lacks a membrane-spanning region and a cytoplasmic domain. Most of these truncated receptors are secreted from the cell, but some of them remain associated with the outer surface of the cell. In this position they can bind LDL, but the lack of a cytoplasmic domain renders these receptors incapable of clustering into coated pits and carrying LDL into the cell.

Southern Blot Analysis of FH 274 DNA Relative To Normal DNA

The preferred mode contemplated by the present inventors for displaying a deletion mutation in an FH individual involves the use of a well-known technique known as Southern blotting. Briefly, Southern blotting is a procedure whereby genomic DNA from an individual is first isolated and fragmented into discrete fragments and separated electrophoretically on an agarose gel. The pattern of DNA from the gel may then be "imprinted" onto a stable matrix. The pattern of those fragments which correspond to the LDL receptor gene may then be visualized by hybridizing a labeled LDL receptor cDNA or genomic probe with the imprinted matrix and visualizing the gene pattern by means of the label.

In performing the initial DNA fragmentation, the DNA is preferrably restriction endonuclease digested into smaller DNA fragments. However, the only requirement is that the method chosen should be able to cleave the genomic DNA reproducibly into the same fragment pattern. In this manner, identically cleaved gene fragments will exhibit a reproducible pattern when separated, for instance, on the basis of fragment length. Thus, LDL receptor gene fragments from test individuals might be compared to the corresponding fragments from control individuals to detect a shift in the respective LDL gene pattern. A shift in the pattern of LDL receptor gene fragments from a test individual relative to a control pattern would be indicative of a mutation in the gene.

The present inventors have determined that the restriction endonuclease Xba I was capable of displaying the genetic mutation exhibited by FH 274. However, it is contemplated that in future case studies, it may become necessary to use other restriction enzymes. Thus, a battery of enzymes may be useful in certain instances to find the correct enzyme for that particular defect. Those of skill in the art will recognize that such a battery of digestions may be necessary.

After fragmenting the DNA, the fragments produced are then separated into a pattern whereby individual fragments are separated from one another. The preferable means for separating the DNA fragments is to separate the fragments according to size by subjecting the DNA to electrophoresis in an agarose gel matrix. Agarose gel electrophoresis is a procedure well-known in the art. However, other types of separation techniques may be used, including, for example, column chromatogarphy or density gradient centrifugation. The gel electrophoresis technique is useful in that it allows the separation of fragments in a manner which allows for precise determination of the apparent size of the separated fragments and allows for easy handling of the fragments so separated. Furthermore, the LDL receptor gene fragments which are present in the gel matrix may be directly visualized by the Southern blotting technique described more fully below.

Figures 4A, 4B:
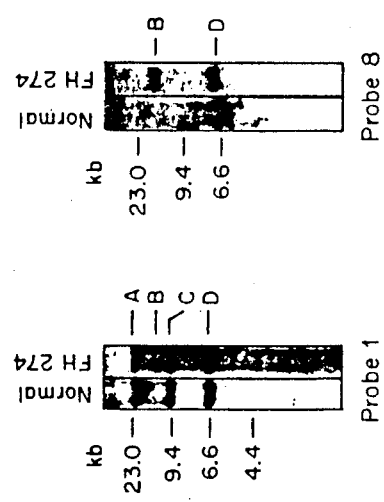
FIG. 4A is a diagram of the mRNA for the human LDL receptor which is shown with AUG and UGA indicating the beginning and end of the translated region, respectively. The sizes and locations of the $^{32}$P-labeled cDNA probes used to map the LDL receptor gene are shown by the closed bars and are numbered 1-9.
FIG. 4B is an autoradiograph of a Southern blot of either normal or mutant (FH 274) genomic DNA following hybridization with either probe 1 (left) or probe 8 (right). The Xba I restriction fragments are designated A-D along the right side of each blot. Molecular size standards were generated by Hind III cleavage of bacteriophage DNA and are indicated to the left of each blot. The Xba I fragments detected by probes 2-9 in the normal subject and FH 274 are indicated at the bottom of FIG. 4A.

FIG. 4B shows Southern blots of genomic DNA from normal cells and from FH 274, after digestion with Xba I, and hybridization with several cDNA probes. More particularly, the Southern blot hybridizations were performed as follows. Genomic DNA (4 ug) was isolated from cultured fibroblasts from the indicated subject (Maniatis, supra.), digested with XbaI (New England Biolabs), electrophoresed in 1% agarose containing buffer A (40 mM Tris-acetate, 3 mM Na$_2$EDTA, 20 mM NaOAc, and 18 mM NaCL at pH 8.15), and transferred to nitrocellulose paper by osmotic diffusion (Maniatis, supra). The paper was incubated for 16 hours at 42° C. with the appropriate $^{32}$P-labeled cDNA probe (2-4×10$^6$ cpm/ml) in 50% formamide, 1% SDS, 5x Denhardt's solution, 5×SSPE, and 100 ug/ml E. coli DNA after prehybridization for 1 hour at 42° C. in the same solution without the $^{32}$P-labeled probe. After hybridization, the paper was washed in 1% SDS plus 2×SSC for 15 minutes at 23° C. and then in 1% SDS plus 0.1×SSC (for probe 1 hybridizations) or in 1% SDS plus 0.5×SSC (for probes 2-9) for 4 hours at 68° C. Filters were exposed to X-ray film with an intensifying screen for 24 hours at −70° C. Two representative blot hybridizations using probes 1 and 8 are shown in FIG. 4B.

The sizes and locations of $^{32}$P-labeled cDNA probes used to map the LDL receptor gene are shown in FIG. 4A by the closed bars and are numbered 1 to 9. Probe 1 (double-stranded DNA) was a mixture of a 2.1-kb EcoRI-SmaI fragment and three different 0.9-kb BamHI-XhoI fragments from p101, which together spanned most of the translated region of the gene. The fragments were purified by polyacrylamide gel electrophoresis and electroelution and then labeled with $^{32}$P by random hexanucleotide priming as described by Feinberg and Vogelstein, Analyt. Biochem, 132:6-13 (1983), incorporated herein by reference. Probes 2 through 9 were prepared from M13 subclones of pLDLR-2 as a single-stranded, uniformly $^{32}$P-labeled DNA approximately 100 nucleotides in length by the method of Church and Gilbert, Proc. Natl. Acad. Sci. USA. 81:1991-1995 (1984), incorporated herein by reference. All probes had a specific radioactivity of at least 5×10$^8$ cpm/ug.

Briefly, to prepare probe 2 a DNA fragment encompassing nucleotides 267 to 1081 (FIG. 3) was cloned into the bacteriophage M13mp9 vector as described by Messing, Meth. Enzymol., 101:20-78 (1983), incorporated herein by reference. Single-stranded, uniformly $^{32}$P-labeled DNA probes approximately 100 bases long were prepared from the resulting clone by the method of Church and Gilbert, supra. using an M13 universal primer and the Klenow fragment of DNA polymerase I to extend the primer in the presence of three unlabeled deoxynucleotides and one alpha×$^{32}$P-labeled deoxynucleotide. The resulting radioactive primer extension product was denatured from the template by boiling, size-fractionated on a denaturing acrylamide gel, electroeluted, and then used directly as a probe. Probes 3-9 were prepared in a similar manner, except M13 clones containing different regions of the sequence in FIG. 3 were used as templates.

Referring to FIG. 3, probe 3 encompasses approximately nucleotides number 719 to 2544; Probe 4 encompasses approximatley nucleotides 267 to 1078; Probe 5 encompasses approximately nucleotides 1573 to 3486; Probe 6 encompasses approximately nucleotides 2154 to 2544; Probe 7 encompasses approximately 2545 to 3948; and Probes 8 and 9 encompass approximately 4508 to 4962.

FIG. 4B shows Southern blots of genomic DNA from normal cells and from FH 274 after digestion with XbaI and hybridization with several cDNA probes. Probe 1 was a mixture of cDNA fragments that spanned most of the translated region of the LDL receptor mRNA (FIG. 4A). When this probe was hybridized to the XbaI-digested genomic DNA from the normal subject, three bands were observed, of 23-, 10-, and 7-kb, designated A, C, and D, respectively (FIG. 4B). All of these normal bands plus one additional band of 13-kb, designated B, were present in the genomic DNA of FH 274. These findings suggest that one of the mutant alleles in FH 274 has a normal restriction pattern whereas the other allele gives rise to band B.

To localize the DNA segment that gives rise to band B, the XbaI digests were probed with short DNA fragments that corresponded to discrete regions of the LDL receptor cDNA (probes 2-9, FIG. 4A). Probes 2 to 5 hybridized to identical bands in normal and FH 274 DNA. Probes 6, 8 and 9 (but not probe 7) hybridized to the abnormal 13-kb band B in the FH 274 DNA. Inasmuch as band B does not hybridize with probe 7 but does hybridize with probes on either side of probe 7 (that is, probes 6, 8, and 9), this fragment appears to result from a deletion of DNA that includes the region encoding the mRNA encompassed by probe 7. This deletion would presumably involve the removal of at least one XbaI site with fusion of the adjacent DNA sequences into a single XbaI fragment of 13 kb, namely band B.

The specific mutation exhibited by FH 274 should in no way be construed as the only type of mutation that will be found in other FH individuals. Therefore, although probes 2 through 5 failed to demonstrate an altered LDL receptor gene fragment pattern in the case of FH 274, these probes will be useful in detecting other mutations in other FH individuals. Probes 2 through 5 hybridize to the 5' half of the receptor gene. Therefore, mutations which occur in this region of the receptor gene will be detectable using probes 2 through 5. Similarly, since probe 7 hybridizes to band D (FIG. 4A), it will be useful in detecting mutations which occur in this gene region.

Figure 5:
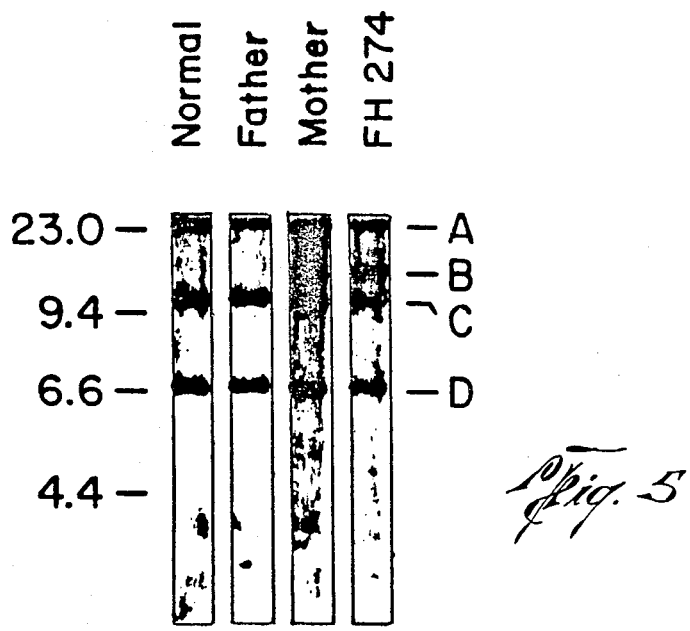
FIG. 5 is a Southern blot hybridization of XbaI-cleaved genomic DNA from a normal subject, FH 274 and his parents. Genomic DNA (5 µg) isolated from cultured fibroblasts from the indicated subject was digested with XbaI, electrophoresed, transferred to nitrocellulose, and hybridized with $^{32}$P-probe 1. The four relevant XbaI restriction fragments are designated A-D along the right side of the blot. Molecular size standards were generated by HindIII cleavage of bacteriophage λDNA.

To determine whether band B originated from the maternal (internalization-defective) or paternal (null) allele, we performed XbaI digests of genomic DNA from the two parents. FIG. 5 shows that band B was present in the DNA from the mother, but not the father, indicating that the deletion was present on the internalizationdefective allele.

Detailed Characterization of the Mutation Exhibited by FH 274

The following set of experiments demonstrate the utility of the present invention in being able to detect the presence of a mutation in the LDL receptor gene and in providing the means whereby such mutation may be specifically detailed and identified.

By using genomic recombinant clones and Southern blotting techniques with LDL receptor cDNA probes, a detailed restriction map of an FH individual can be generated. These gene mapping techniques are now wellknown to those of skill in the art. The particular map generated for FH 274 is displayed in FIG. 6. FIG. 6 is a comparison of restriction maps of the 3' end of the normal LDL receptor gene and the deletion-bearing gene from FH 274. The scale at the bottom indicates the length of genomic DNA in kilobases. The organization of the normal LDL receptor gene is shown in the diagram at the top. Exons are indicated by solid segments and upper case letters; intervening sequences (IVS) are indicated by open segments and lower case letters. The Alu repetitive sequences in IVS c and Exon F are indicated. Restriction enzyme recognition sites used to define the gene deletion in FH 274 are shown.

The restriction map of the normal receptor gene was generated from studies of three genomic clones (λ33-2, λ33-1, λh1) (Example III). The map of the gene in FH 274 was generated from λFH 274-10, which contains XbaI fragment B (FIGS. 4B and 5) (see below). Solid bars above or below the restriction maps denote segments of the normal and mutant genes that were used for DNA sequencing.

To obtain λFH 274-10, we prepared 570 ug of genomic DNA from fibroblasts of FH 274 and digested it with 1700 units XbaI. The digested DNA was extracted with phenol/chloroform and then chloroform, precipitated with 70% ethanol and 86 mM sodium acetate, and dissolved in 200 ul of buffer B (10 mM Tris-chloride and 1 mM Na$_2$EDTA at pH 7.5). The DNA (80 ug) was redigested with 100 units XbaI, loaded onto a 1% low-gelling temperature agarose gel (Bethesda Research Laboratories) containing buffer A, and electrophoresed at 40 V for 72 hr at 4° C. After electrophoresis, ten 2-mm slices of the gel containing DNA fragments ranging from 9 to 23 kb were extracted, concentrated, and dissolved in 20 ul of buffer B. One aliquot (4 ul) of each DNA fraction, 5 ug of XbaI-digested genomic DNA from FH 274, and size marker fragments were loaded onto individual lanes of a 0.8% agarose gel containing buffer A and electrophoresed at 35 V for 16 hours at 23° C.

The DNA was transferred to nitrocellulose paper and hybridized with $^{32}$P-labeled probe 1 as described above. The resulting autoradiogram identified the fraction that contained the abnormal 13-kb XbaI fragment (fragment B, FIG. 4). The remaining DNA from this fraction (100 ng) was mixed with 500 ng of XbaI-digested arms of λ Charon 35 and incubated with 490 units of T4 DNA ligase (New England Biolabs) for 72 hours at 14° C. The ligated material was packaged into λ phage particles in vitro (Amersham) to yield a total of 6.7×10$^3$ plaque forming units. This library was screened with $^{32}$P-labeled probe 8 (FIG. 1), which was expected to detect only the abnormal fragment (13 kb), since the corresponding normal fragment ( 7 kb) was too small to generate viable recombinant phage. One recombinant clone was identified (λFH 274-10) and isolated after an additional cycle of plaque purification. The ( 13-kb insert in λFH 274-10 was isolated from purified DNA, subcloned into pSP65 (Promega Biotec), and used for restriction endonuclease mapping.

FIG. 6 demonstrates that the PvuII site in IVSc and the SstI site in Exon F were separated by approximately 5.9-kb in the cloned fragments of the normal gene but only by approximately 0.6-kb in the cloned fragment of the FH 274 gene. Moreover, several restriction enzyme sites between the PvuII site and the SstI site are shown to be missing from the cloned FH 274 gene. These data confirmed the diagnosis made from the genomic Southern blots discussed above and further suggested that 5 kb of DNA was deleted from the FH 274 gene. The deletion included the 3' end of IVS c, all of Exons D and E and the IVS's separating them, and the 5' end of Exon F.

To locate precisely the 5' and 3' breakpoints and the structure at the deletion joint in FH 274, we determined the nucleotide sequences of the cloned portions of the genes delimited by the bars in FIG. 6. These sequences revealed that the deletion joint occurred between two repetitive elements of the Alu family that were oriented in opposite directions. The 5' side of the deletion joint was derived from an Alu sequence in IVS c. The 3' side of the deletion joint was derived from an oppositely-oriented Alu sequence in Exon F.

A test performed on a second FH individual using the present invention failed to reveal a deletion in the LDL receptor gene of that individual. It is felt that the defect in the LDL receptor gene of this individual is due to a point mutation. Defects which are not due to a deletion mutation can be detected by modification and extentions of the present invention which will be described in future applications.

Although recombination between repetitive DNA sequences has been postulated to be a cause of deletions, to the knowledge of the present inventors such rearrangements have not previously been reported in eukaryotic cells. In the most well characterized set of mammalian deletion mutations, i.e., those that occur in the human alpha- and beta-globin genes, one of the deletion breakpoints frequently occurs within an Alu sequence but the other breakpoint thus far has always occurred in a nonrepetitive sequence of DNA.

The present invention has been disclosed in terms of examples considered by the inventors to be the preferred methods for practicing the invention. However, they are in no way meant to be the only modes of practicing this invention. For example, although the restriction enzyme XbaI was useful in exhibiting the particular mutation carried by FH 274, it is contemplated that the use of other restriction protocols may be necessary to display the specific mutation in other FH individuals. Similarly, although the present inventors feel that the Southern blot technique represents the best mode for displaying the pattern of LDL receptor gene fragments, other techniques should also work and should be considered as included within the scope of the present invention. For example, it would be possible to separate the fragments by column chromatography and assaying for the presence of gene fragments as they elute from the column. Similarly, although the probes used in the practice of the present invention have been radiolabeled, it is not considered that radiolabeling is the only technique whereby the probes may be rendered detectable. For example, DNA hybridization probes may be labeled with heavy isotopes or, alternatively, by binding a ligand such as biotin. In general, any specifically bindable ligand that is capable of being independently detected can be used. These and all other changes should be considered within the scope of the appended claims.

Although the particular case disclosed was a mutation resulting from a deletion, further extensions of the present invention can also detect mutations resulting from other types of events, including single nucleotide changes. The latter can be detected directly on Southern gel blots when they lead to the loss or acquisition of a resriction enzyme cleavage site. Single nucleotide changes can also be detected by their reduced hybridization with short segments of the cDNA for chemically synthesized oligonucleotides corresponding to the sequence of the cDNA. Weakened hybridization can be detected by the "melting" or dissociation of the mutant and normal DNA sequences after they have been hybridized to each other. Such abnormal melting behavior can be detected as an increased sensitivity to heat, lower ionic strength, or chemicals such as urea and formamide that dissociate chains of hybridized DNA. Thus, the present invention will be useful for the diagnosis of all potential mutations in the LDL receptor gene.

What is claimed is:

1. A DNA molecule comprising a recombinant DNA vector having a DNA sequence which encodes human LDL receptor protein as defined by the amino acid sequence of FIGS. 3A, 3B, 3C and 3D.

2. The DNA molecule of claim 1 wherein the recombinant vector comprises at least the translated region of the cDNA insert of plasmid pLDLR-2, ATCC deposit number 39966.

3. A substantially purified DNA molecule comprising a DNA sequence which encodes human LDL receptor protein as defined by the amino acid sequence of FIGS. 3A, 3B, 3C and 3D.

4. A bacterial strain comprising a recombinant DNA vector which includes the recombinant insert of pLDLR-2, lambda 33-1, lambda 33-2 or lambda h1, ATCC deposit numbers 39966, 40147, 40148 and 40149, respectively.

5. A DNA molecule comprising a recombinant DNA vector which includes the recombinant insert of pLDL-2, lambda 33-1, lambda 33-2, or lambda h1, ATCC deposit numbers 39966, 40147, 40148 and 40149, respectively.

6. A substantially purified DNA molecule consisting of at least a tetradecameric portion of the DNA sequence of FIGS. 3A, 3B, 3C or 3D.

7. A substantially purified DNA molecule comprising a DNA sequence which includes at least a tetradecameric portion of the DNA sequence of FIGS. 3A, 3B, 3C or 3D, the DNA molecule being capable of hybridizing to the recombinant insert of pLDLR-2, lambda 33-1, lambda 33-2 or lambda h1, ATCC deposit numbers 39966, 40147, 40148 and 40149, respectively, under stringent hybridization conditions, said conditions including hybridization in the presence of 50% formamide and $5 \times$ SSPE at 42 degrees C.

8. The DNA molecule of claim 7 wherein the DNA sequence comprises the cDNA insert of plasmid pLDLR-2, ATCC deposit number 39966.

9. The DNA molecule of claim 7 wherein the DNA sequence comprises the recombinant DMA insert of bacteriophage lambda 33-1, ATCC deposit number 40147.

10. The DNA molecule of claim 7 wherein the DNA sequence comprises the recombinant DNA insert of bacteriophage lambda 33-2, ATCC deposit number 40148.

11. The DNA molecule of claim 7 wherein the DNA sequence comprises the recombinant DNA insert of bacteriophage lambda h1, ATCC deposit number 40149.

12. The DNA molecule of claim 7 wherein the DNA sequence comprises the translataed region of the cDNA sequence of FIGS. 3A, 3B, 3C or 3D.

13. The DNA molecule of claim 7 wherein the DNA sequence comprises nucleotides 267 to 1081 of the cDNA sequence of FIGS. 3A and 3B.

14. The DNA molecule of claim 7 wherein the DNA sequence comprises nucleotides 719 to 2544 of the cDNA sequence of FIGS. 3A, 3B, 3C and 3D.

15. The DNA molecule of claim 7 wherein the DNA sequence comprises nucleotides 267 to 1078 of the cDNA sequence of FIGS. 3A and 3B.

16. The DNA molecule of claim 7 wherein the DNA sequence comprises nucleotides 1573 to 3486 of the cDNA sequence of FIGS. 3A, 3B, 3C and 3D.

17. The DNA molecule of claim 7 wherein the DNA sequence comprises nucleotides 2154 to 2544 of the cDNA sequence of FIGS. 3A, 3B, 3C and 3D.

18. The DNA molecule of claim 7 wherein the DNA sequence comprises nucleotides 2545 to 3948 of the cDNA sequence of FIGS. 3C and 3D.

19. The DNA molecule of claim 7 wherein the DNA sequence comprises nucleotides 4508 to 4962 of the cDNA sequence of FIGS. 3C and 3D.

20. A DNA molecule comprising a recombinant DNA vector having a recombinant DNA insert which includes the DNA molecule of any one of claims 7,6 or 9-19.

21. A bacterial strain bearing a recombinant DNA vector having a recombinant DNA insert defined by the DNA molecule of any one of claims 6-19.

* * * * *

UNITED STATES PATENT AND TRADEMARK OFFICE
CERTIFICATE OF CORRECTION

PATENT NO. : 4,745,060

DATED : May 17, 1988

INVENTOR(S) : Michael S. Brown et al

It is certified that error appears in the above-identified patent and that said Letters Patent is hereby corrected as shown below:

Column 22, line 18, "DMA" should read -- DNA --.

Column 22, line 30, "translataed" should read -- translated --.

Signed and Sealed this

Fourteenth Day of February, 1989

Attest:

DONALD J. QUIGG

Attesting Officer

Commissioner of Patents and Trademarks